United States Patent
Maehr (12)

(10) Patent No.: US 6,232,471 B1
(45) Date of Patent: May 15, 2001

(54) SYNTHESIS OF ANTI-INFLAMMATORY [1,2,3]TRIAZOLES

(75) Inventor: Hubert Maehr, Wayne, NJ (US)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 09/443,397

(22) Filed: Nov. 19, 1999

Related U.S. Application Data

(60) Provisional application No. 60/109,446, filed on Nov. 23, 1998.

(51) Int. Cl.$^7$ ................................................ C07D 249/06
(52) U.S. Cl. ................................................ 548/255
(58) Field of Search ................................................ 548/255

(56) References Cited

U.S. PATENT DOCUMENTS

| | | |
|---|---|---|
| 3,644,343 | 2/1972 | Manning . |
| 3,726,868 | 4/1973 | Manning . |
| 4,908,363 | 3/1990 | Klötzer et al. . |
| 5,523,310 | 6/1996 | Maehr . |

*Primary Examiner*—Patricia L. Morris
(74) *Attorney, Agent, or Firm*—George W. Johnston; Patricia S. Rocha-Tramaloni; Robert A. Silverman

(57) ABSTRACT

This invention relates to new processes for manufacturing 4-[3,5-bis(1,1-dimethylethyl)-4-hydroxyphenyl]-N-methyl-3H-[1,2,3]triazole-5-carboxamide (compound I) as well as the following new intermediates useful in these synthetic processes. 2-benzenesulfonyl-N-methylacetamide (compound IV), 2-(benzenesulfonyl)-3-[3,5-bis(1,1-dimethylethyl)-4-hydroxyphenyl]-N-methylacrylamide (compound II) and threo-2-[2-benzenesulfonyl-1-[3,5-bis(1,1-dimethylethyl)-4-hydroxyphenyl]-2-[(methylcarbamoyl)ethyl]]-5-[3,5-bis(1,1-dimethylethyl)-4-hydroxyphenyl]-N-methyl-2H-[1,2,3]triazole-4-carboxamide (compound III).

1 Claim, No Drawings

SYNTHESIS OF ANTI-INFLAMMATORY [1,2,3]TRIAZOLES

This application claims priority of U.S. Provisional Application No. 60/109,446 filed Nov. 23, 1998.

FIELD OF THE INVENTION

The present invention relates to processes for the manufacture of the following compound, 4-[3,5-bis(1,1-dimethylethyl)-4-hydroxyphenyl]-N-methyl-3H-[1,2,3]triazole-5-carboxamide, compound (I).

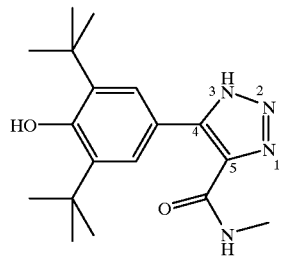

I

This compound and its 1H-tautomer and pharmaceutically acceptable salts are known in U.S. Pat. No. 5,523,310, incorporated herein by reference.

BRIEF SUMMARY OF THE INVENTION

The invention relates to processes for the preparation of compound (I). In one aspect, the invention relates to a process for preparing 4-[3,5-bis(1,1-dimethylethyl)-4-hydroxyphenyl]-N-methyl-3H-[1,2,3]triazole-5-carboxamide comprising:

a) reacting methyl phenylsulfonylacetate with methylamine to yield 2-benzenesulfonyl-N-methylacetamide;

b) condensing 3,5-bis(1,1-dimethylethyl)-4-hydroxybenzaldehyde with the product of step a) to yield 2-(benzenesulfonyl)-3-[3,5-bis(1,1-dimethylethyl)-4-hydroxyphenyl]-N-methylacrylamide; and c) reacting the product of step b) with a metal azide to yield 4-[3,5-bis(1,1-dimethylethyl)-4-hydroxyphenyl]-N-methyl-3H-[1,2,3]triazole-5-carboxamide.

In another aspect, the invention relates to a process for preparing 4-[3,5-bis(1,1-dimethylethyl)-4-hydroxyphenyl]-N-methyl-3H-[1,2,3]triazole-5-carboxamide comprising:

reacting threo-2-[2-benzenesulfonyl-1-[3,5-bis(1,1-dimethylethyl)-4-hydroxyphenyl]-2-[(methylcarbamoyl)ethyl]]-5-[3,5-bis(1,1-dimethylethyl)-4-hydroxyphenyl]-N-methyl-2H-[1,2,3]triazole-4-carboxamide with a metal azide to yield 4-[3,5-bis(1,1-dimethylethyl)-4-hydroxyphenyl]-N-methyl-3H-[1,2,3]triazole-5-carboxamide.

In another aspect, the invention relates to a process for preparing 4-[3,5-bis(1,1-dimethylethyl)-4-hydroxyphenyl]-N-methyl-3H-[1,2,3]triazole-5-carboxamide comprising:

reacting 2-(benzenesulfonyl)-3-[3,5-bis(1,1-dimethylethyl)-4-hydroxyphenyl]-N-methylacrylamide with a metal azide to yield 4-[3,5-bis(1,1-dimethylethyl)-4-hydroxyphenyl]-N-methyl-3H-[1,2,3]triazole-5-carboxamide.

In another aspect, the invention also relates to the following synthetic intermediates used in the preparation of compound (1).

A compound having the structure

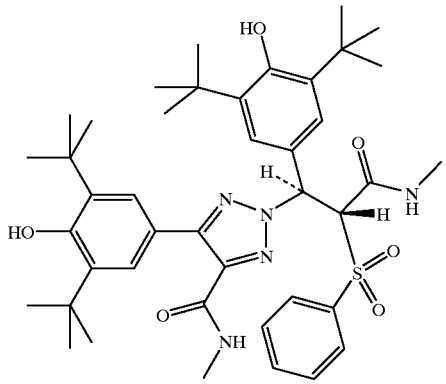

III threo-2-[2-benzenesulfonyl-1-[3,5-bis(1,1-dimethylethyl)-4-hydroxyphenyl]-2-[(methylcarbamoyl)ethyl]]-5-[3,5-bis(1,1-dimethylethyl)-4-hydroxyphenyl]-N-methyl-2H-[1,2,3]triazole-4-carboxamide.

A compound having the structure

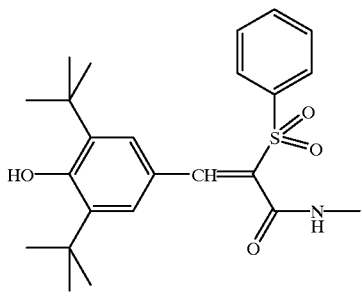

II 2-(benzenesulfonyl)-3-[3,5-bis(1,1-dimethylethyl)-4-hydroxyphenyl]-N-methylacrylamide; and a compound having the structure

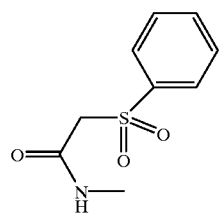

IV benzenesulfonyl-N-methylacetamide.

In one other aspect, this invention relates to a method for preparing the carboxamide I, comprising of reacting compound (II), 2-(benzenesulfonyl)-3-[3,5-bis(1,1-dimethylethyl)-4-hydroxyphenyl]-N-methylacrylamide,

II

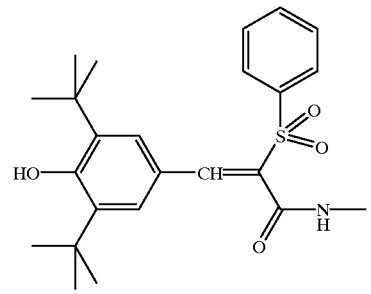

with sodium azide to form an intermediate condensation product, threo-2-[2-benzenesulfonyl-1-[3,5-bis(1,1-dimethylethyl)-4-hydroxyphenyl]-2-[(methylcarbamoyl)ethyl]]-5-[3,5-bis(1,1-dimethylethyl)-4-hydroxyphenyl]-N-methyl-2H-[1,2,3]triazole-4-carboxamide, compound (III),

III

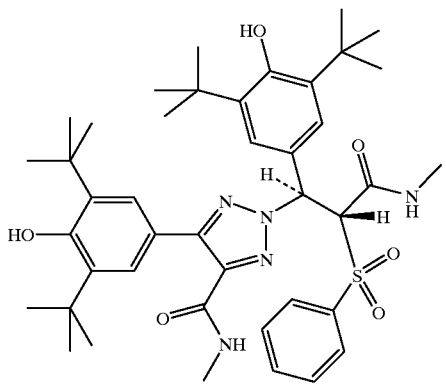

The carboxamide compound (III) will further react with sodium azide to form the carboxamide (I).

In all instances, preferably the metal azide is lithium, potassium or sodium azide, most preferably, sodium azide.

DETAILED DESCRIPTION OF THE INVENTION

The invention relates to methods for the manufacture of 4-[3,5-bis(1,1-dimethylethyl)-4-hydroxyphenyl]-N-methyl-3H-[1,2,3]triazole-5-carboxamide (I) and intermediates for the manufacture of the same.

REACTION SCHEME A

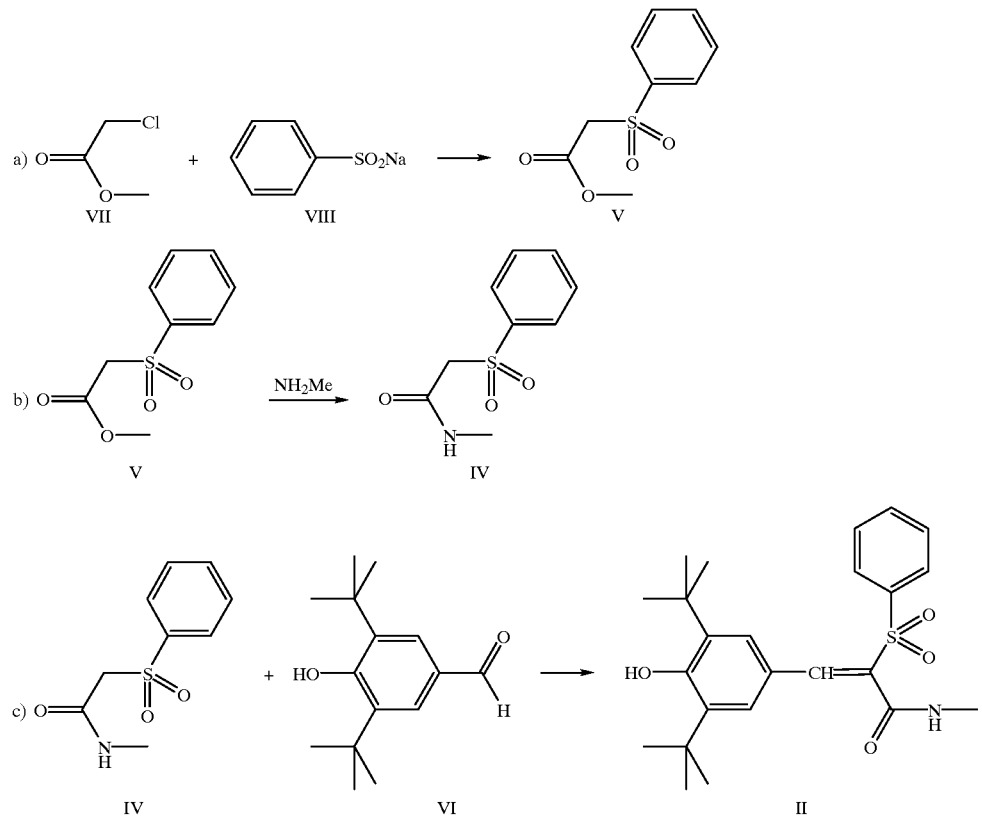

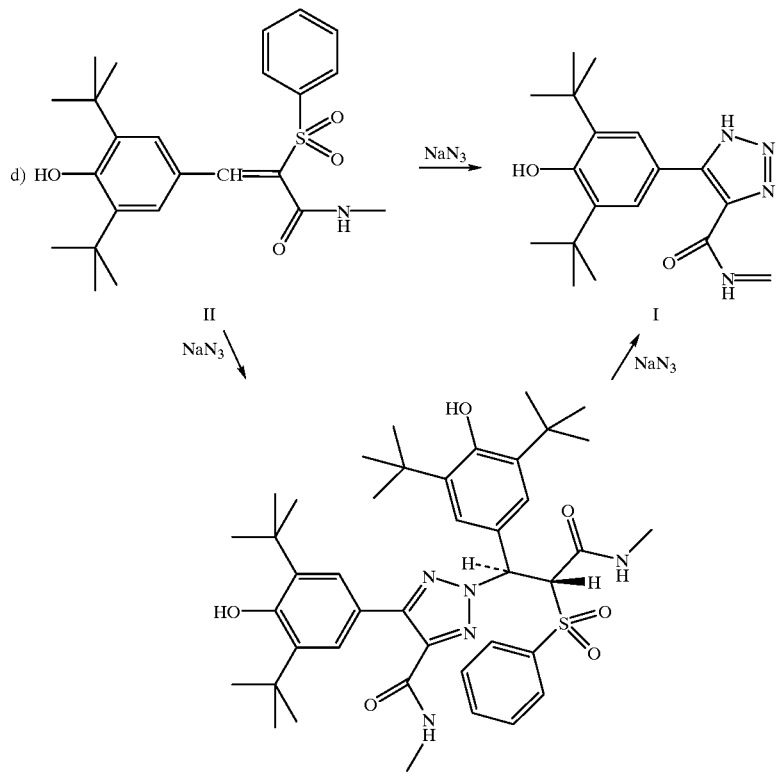

REACTION SCHEME B

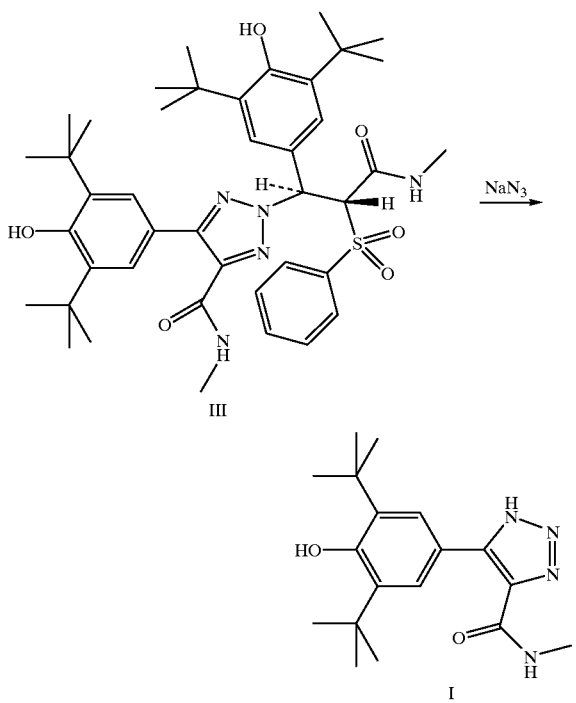

In Reaction Scheme A, step a) phenylsulfonylacetic acid methyl ester (V), is prepared from known starting materials comprising methyl chloroacetate (VII), and benzenesulfinic acid, sodium salt (VIII), or materials which can be prepared readily according to methods which are known to persons skilled in the synthetic arts. Such a method for preparing the starting ester (V) is disclosed in Reaction Scheme II in U.S. Pat. No. 5,523,310.

The recovered ester V of step a) may be converted to the corresponding amide (IV), of step b) by reacting said ester with methylamine, most conveniently 40% aqueous methylamine. The ester-amide conversion reaction can be performed at temperature ranges of about 10° C. to about 80° C., most preferably at room temperature.

The Knoevenagel reaction of step c) can be conducted, for example, in refluxing toluene or toluene-cyclohexane mixtures in the presence of 1-methylpiperazine. Other hydrocarbon solvents and solvent mixtures such as benzene, xylene, hexane, toluene, and heptane and other bases commonly used in Knoevenagel reaction, known by synthetic practitioners can be employed. This reaction condenses intermediate 2-benzenesulfonyl-N-methylacetamide (IV) with commercially available 3,5-bis(1,1-dimethylethyl)-4-hydroxybenzaldehyde (VI) to yield the intermediate 2-(benzenesulfonyl)-3-[3,5-bis(1,1-dimethylethyl)-4-hydroxyphenyl]-N-methylacrylamide (II).

In step d), 2-(benzenesulfonyl)-3-[3,5-bis(1,1-dimethylethyl)-4-hydroxyphenyl]-N-methylacrylamide (II), is reacted with a metal azide, preferably an alkali metal azide such as lithium, potassium or sodium azide, most preferably sodium azide, in solvents such as 2-methoxyethanol, 1-propanol, 2-propanol, butanol, N,N-dimethylformamide, dimethyl sulfoxide and the like, most preferably 2-methoxyethanol at temperatures of about 60° to about 160° C. for about 25 to about 35 hours, most preferably at about 100° C. for about 30 hours.

The reaction of methylacrylamide (II), with sodium azide in the procedure of the present invention does not produce the desired product 4-[3,5-bis(1,1-dimethylethyl)-4-hydroxyphenyl]-N-methyl-3H-[1,2,3]triazole-5-carboxamide (I) directly, but initially yields substantial quantities of threo-2-[2-benzenesulfonyl-1-[3,5-bis(1,1-dimethylethyl)-4-hydroxyphenyl]-2-[(methylcarbamoyl)ethyl]]-5-[3,5-bis(1,1-dimethylethyl)-4-hydroxyphenyl]-N-methyl-2H-[1,2,3]triazole-4-carboxamide (III). This condensation product of compound (II), and the desired [1,2,3]triazole-5-carboxamide (I), can be isolated by conventional methods.

Starting directly from pure threo-2-[2-benzenesulfonyl-1-[3,5-bis(1,1-dimethylethyl)-4-hydroxyphenyl]-2-[(methylcarbamoyl)ethyl]]-5-[3,5-bis(1,1-dimethylethyl)-4-hydroxyphenyl]-N-methyl-2H-[1,2,3]triazole-4-carboxamide (III), and reacting with an excess of a metal azide such as lithium, potassium, or sodium azide it is also possible to obtain 4-[3,5-bis(1,1-dimethylethyl)-4-hydroxyphenyl]-N-methyl-1H-[1,2,3]triazole-5-carboxamide (1), according to reaction Scheme B.

The carboxamide (III) is thus a precursor for the production of the anti-inflammatory product (I)

EXAMPLE 1
Preparation of Phenylsulfonylacetic Acid, Methyl Ester.

A 3-L three-neck round-bottom flask, equipped with mechanical stirrer, reflux condenser, nitrogen bubbler, heating mantle and thermometer, was charged with 328 g (3.02 mol) of methyl chloroacetate and 600 mL of dimethylformamide. The stirred solution was heated to 60° C. At this time 504 g (3.07 mol) of benzenesulfinic acid, sodium salt was added, over a period of 10 min to control the exothermic reaction. During the addition process the internal reaction temperature was not allowed to exceed 130° C. The stirred reaction mixture was maintained between 130 to 135° C. for 3 h, followed by slow cooling to 30° C. over a period of 2 h. The cooled mixture was diluted with 500 ml of deionized water and 500 g of ice. The resulting two phase mixture was maintained at 5° C. and stirred at that temperature for 1 h. At this time, the crystallization of methyl phenylsulfonylacetate was induced and was allowed to proceed for an additional hour with stirring. A second addition of 100 g of ice then followed, and stirring continued for 1 h. The resulting suspension was vacuum filtered through a chilled Buchner funnel. The isolated filter cake was washed with 2×350 mL portions of cold water. Most of the residual water was removed by vacuum. This process resulted in the isolation of 775 g of crude phenylsulfonylacetic acid, methyl ester (V).

EXAMPLE 2
Preparation of 2-benzenesulfonyl-N-methyl acetamide (IV).

The entire isolated, crude and moist phenylsulfonylacetic acid methyl ester (V) was transferred to a 2-L Erlenmeyer flask and dissolved in 1 L (11.7 mol) of 40% aqueous methylamine. The reaction temperature rose to 30° C. The mixture was allowed to cool to ambient temperature, and was maintained at this temperature for an additional hour, followed by cooling overnight in a refrigerator. The precipitate product (IV) was removed by filtration. The filter cake was washed with 3×300 mL of cold water. Drying the recovered white solid at 60° C. at 30 torr over potassium hydroxide flakes for 27 h yielded 402.7 g of the methylacetamide (IV), 97.3% purity by HPLC, mp 106–109° C.

EXAMPLE 3
3a. Preparation of 2-(benzenesulfonyl)-3-[3,5-bis(1,1-dimethylethyl)-4-hydroxyphenyl]-N-methylacrylamide (II).

A 1-L three neck-round-bottom flask equipped with a mechanical stirrer, thermometer, reflux condenser, Dean Stark trap and nitrogen bubbler was charged with 53.3 g (0.250 mol) of 2-benzenesulfonyl-N-methyl acetamide, 64 g (0.263 mol) of 3,5-bis(1,1-dimethylethyl)-4-hydroxybenzaldehyde hemihydrate, 5 mL (0.045 mol) of 1-methylpiperazine, and 500 mL of toluene. The mixture was refluxed for 70 h. The heating mantel was removed and crystallization was allowed to proceed. After 250 mL of hexane was added to the mixture, the suspension was cooled to 5° C. for 1 h, then filtered. The filter cake was first washed with 3×80 mL of 3:2 toluene: hexane, followed by 100 mL of petroleum ether. The off-white solid material was dried at 55° C. under high vacuum for 4 h to afford 96.2 g of crude (II), 2-(benzenesulfonyl)-3-[3,5-bis(1,1-dimethylethyl)-4-hydroxyphenyl]-N-methylacrylamide, 97% purity by HPLC.

3b. Recrystallization of 2-(benzenesulfonyl)-3-[3,5-bis(1,1-dimethylethyl)-4-hydroxyphenyl]-N-methylacrylamide(II).

A 1-L three neck-round-bottom flask equipped with a mechanical stirrer, thermometer, reflux condenser and nitrogen bubbler was charged with 96 g of crude 2-(benzenesulfonyl)-3-[3,5-bis(1,1-dimethylethyl)-4-hydroxyphenyl]-N-methylacrylamide (II), 210 mL of methanol and 20 mL of toluene. The mixture was heated at reflux to yield a yellow solution. Water, 105 mL, at 60° C. was added to the toluene methanol solution at 60° C. to precipitate the product. The resulting suspension was cooled overnight at 5° C. then filtered. The crystals were washed with 2×50 mL of a chilled solution of 2:1 methanol: water followed by drying for 24 h in vacuo over potassium hydroxide flakes to yield 89.4 g of white crystals of 2-(benzenesulfonyl)-3-[3,5-bis(1,1-dimethylethyl)-4-hydroxyphenyl]-N-methylacrylamide (II), 99.35% purity by HPLC.

EXAMPLE 4
4a. Preparation of crude 4-[3,5-bis(1,1-dimethylethyl)-4-hydroxyphenyl]-N-methyl-3H-[1,2,3]triazole-5-carboxamide (I).

A 250 mL 3-neck round-bottom flask immersed in an oil bath, equipped with a mechanical stirrer, thermometer, reflux condenser and nitrogen bubbler, was charged with 42.96 g (0.100 mol) of 2-(benzenesulfonyl)-3-[3,5-bis(1,1-dimethylethyl)-4-hydroxyphenyl]-N-methylacrylamide (II), 100 mL of 2-methoxyethanol and 6.83 g (0.105 mol) of sodium azide. The yellow mixture was heated at 105° C. for 30 h. The cooled orange solution was poured onto a mixture of 150 g of ice and 150 mL of deionized water. The yellow suspension was agitated for 1 h at 5° C. The resulting solid precipitate was filtered off and washed with 5×50 mL of cold deionized water. The recovered solids were dried in vacuo over potassium hydroxide flakes to afford yellow solids, 30.2 g of crude product (I), 98.7% purity by HPLC.

4b. First recrystallization of 4-[3,5-bis(1,1-dimethylethyl)-4-hydroxyphenyl]-N-methyl-3H-[1,2,3]triazole-5-carboxamide.

A 500 mL Erlenmeyer flask was charged with 30.2 g of crude 4-[3,5-bis(1,1-dimethylethyl)-4-hydroxyphenyl]-N-methyl-3H-[1,2,3]triazole-5-carboxamide (I) and 200 mL of acetone. The mixture was heated to reflux, then filtered through a fritted glass funnel. The glass funnel was rinsed with 2×10 mL of warm acetone and the resulting solution was added to the initial acetone filtrate. The combined acetone solutions were concentrated by removal of some solvent. After removal of 65 mL of acetone, the product began to crystallize. To this warm acetone mixture 80 mL of toluene was added, causing the precipitated solids to redissolve. Another 65 mL of the solvent was removed and an additional 80 mL of toluene was added to the warm mixture. Another 65 mL of the solvent was collected at a temperature of 95° C. The mixture was allowed to cool slowly to ambient temperature and was then placed in a refrigerator overnight. Filtration of the solid product followed by washing the solids with 15 mL of cold toluene, 2×12 mL of a cold 3:2 toluene: hexane mixture and finally 15 mL of petroleum ether, yielded 29.0 g of off-white crystals of (I), after drying in a high vacuum, 99.9% purity by HPLC.

4c. Second recrystallization of 4-[3,5-bis(1,1-dimethylethyl)-4-hydroxyphenyl]-N-methyl-3H-[1,2,3]triazole-5-carboxamide (I).

A 500 mL three-neck round-bottom flask, fitted with mechanical stirrer, steam bath, thermometer, and reflux condenser was charged with 150 mL ethanol and 29.0 g (87.8 mol) of 4-[3,5-bis(1,1-dimethylethyl)-4-hydroxyphenyl]-N-methyl-3H-[1,2,3]triazole-5-carboxamide, recovered after the initial recrystallization. Heating to reflux caused the dissolution of all material. Refluxing was stopped and 300 mL of deionized water at 60° C. was added to the solution. The resulting mixture was cooled in an ice bath and stirred for an additional hour after an internal temperature of 5° C. was reached, then filtered. The filter cake was washed with 3×35 mL of a chilled 2:1 deionized water: ethanol solution. The remaining white crystals were dried at 60° C. for 20 h over potassium hydroxide under high vacuum to afford 28.55 g of the triazole-5-carboxamide (I) product, 99.9% purity by HPLC.

4d. Third recrystallization of 4-[3,5-bis(1,1-dimethylethyl)-4-hydroxyphenyl]-N-methyl-1H-[1,2,3]triazole-5-carboxamide (I).

A 500 mL, three-neck round-bottom flask, immersed in an oil bath, equipped with a mechanical stirrer, and reflux condenser was charged with 150 mL of ethanol and 28.5 g (86.3 mol) of 4-[3,5-bis(1,1-dimethylethyl)-4-hydroxyphenyl]-N-methyl-1H-[1,2,3]triazole-5-carboxamide obained after two prior recrystallizations. The mixture was refluxed until dissolution of the crystals was complete. To this solution 300 mL deionized water at 65° C. was added. The resulting mixture was brought to ambient temperature, then cooled in an ice bath and filtered. The filter cake was washed with 3×35 mL of cold 2:1 deionized water: ethanol. The resultant white crystals were dried at 80° C. for 20 h under high vacuum yielding 28.20 g of 4-[3,5-bis(1,1-dimethylethyl)-4-hydroxyphenyl]-N-methyl-3H-[1,2,3]triazole-5-carbox-amide (I). 99.9% purity by HPLC.

EXAMPLE 5

5a. Preparation of crude threo-2-[2-benzenesulfonyl-1-[3,5-bis(1,1-dimethylethyl)-4-hydroxyphenyl]-2-[(methylcarbamoyl)ethyl]]-5-[3,5-bis(1,1-dimethylethyl)-4-hydroxyphenyl]-N-methyl-2H-[1,2,3]triazole-4-carboxamide (III).

A 100 mL round bottom flask, equipped with magnetic stirrer, reflux condenser and nitrogen bubbler, was charged with 19.9 g (46.3 mmol) of 2-(benzenesulfonyl)-3-[3,5-bis (1,1-dimethylethyl)-4-hydroxyphenyl]-N-methylacrylamide (II) and 3.3 g (50.9 mmol) of sodium azide and 37 mL of 2-methoxyethanol. The stirred yellow mixture was heated in a bath maintained at 105° C. for 3 h followed by dilution with 50 mL of deionized water. The resulting precipitate was filtered off, washed with 180 mL water followed by overnight drying of the recovered solid at 27 torr over potassium hydroxide flakes. This process yielded 16.34 g of crude threo-2-[2-benzenesulfonyl-1-[3,5-bis(1,1-dimethylethyl)-4-hydroxyphenyl]-2-[(methylarbamoyl)ethyl]]-5-[3,5-bis(1,1-dimethylethyl)-4-hydroxyphenyl]-N-methyl-2H-[1,2,3]triazole-4-carboxamide (III).

5b. Recrystallization of crude threo-2-[2-benzenesulfonyl-1-[3,5-bis(1,1-dimethylethyl)-4-hydroxyphenyl]-2-[(methylcarbamoyl)ethyl]]-5-[3,5-bis(1,1-dimethylethyl)-4-hydroxyphenyl]-N-methyl-2H-[1,2,3]triazole-4-carboxamide (III).

Threo-2-[2-benzenesulfonyl-1-[3,5-bis(1,1-dimethylethyl)-4-hydroxyphenyl]-2-[(methylcarbamoyl)ethyl]]-5-[3,5-bis(1,1-dimethylethyl)-4-hydroxyphenyl]-N-methyl-2H-[1,2,3]triazole-4-carboxamide (III) obtained by the method described above, was dissolved in 40 mL acetone. The solution was filtered and the filtrate was diluted by addition of 45 mL of toluene. The resulting acetone-toluene solution was concentrated. Chilling this concentrate in an ice bath caused crystallization of the product. An additional 10 mL of toluene was added to re-suspend the solidified mass. Filtration of the suspension, followed by washing the recovered solid material with 5 mL of toluene, 25 mL of 3:2 toluene-hexane mixture and finally 25 mL of petroleum ether and drying overnight over potassium hydroxide flakes at 30 torr afforded 11.6 g of crude threo-2-[2-benzenesulfonyl-1-[3,5-bis(1,1-dimethylethyl)-4-hydroxyphenyl]-2-(methylcarbamoyl)ethyl]]-5-[3,5-bis(1,1-dimethylethyl)-4-hydroxyphenyl]-N-methyl-2H-[1,2,3]triazole-4-carboxamide (III) as a cream colored solid. TLC analysis revealed the presence of two components with Rf values of 0.33 (major) and 0.46 (minor).

5c. Second recrystallization of threo-2-[2-benzenesulfonyl-1-[3,5-bis(1,1-dimethylethyl)-4-hydroxyphenyl]-2-(methylcarbamoyl)ethyl]]-5-[3,5-bis(1,1-dimethylethyl)-4-hydroxyphenyl]-N-methyl-2H-[1,2,3]triazole-4-carboxamide (III).

The recovered solid from 5b above was dissolved in 50 mL warm ethanol. An additional 50 mL of water was added to the ethanol solution while heating on a stream bath. The water-ethanol mixture was cooled to room temperature and the precipitated solid was removed by filtration. The recovered solid was washed with 4 mL 1:1 ethanol water. The moist solid was redissolved in 30 mL of ethanol and 20 mL of tetrahydrofuran. Following concentration of the solution, 3 mL of water was added to precipitate a white microcrystalline powder, threo-2-[2-benzenesulfonyl-1-[3,5-bis(1,1-dimethylethyl)-4-hydroxyphenyl]-2-[(methylcarbamoyl)ethyl]]-5-[3,5-bis(1,1-dimethylethyl)-4-hydroxyphenyl]-N-methyl-2H-[1,2,3]triazole-4-carboxamide (III), 5 g after drying for 18 h at 30 torr over potassium hydroxide flakes maintained at 50° C. 99.1% purity by HPLC.

EXAMPLE 6

Preparation of 4-[3,5-bis(1,1-dimethylethyl)-4-hydroxyphenyl]-N-methyl-3H-[1,2,3]triazole-5-carboxamide from threo-2-[2-benzenesulfonyl-1-[3,5-bis(1,1-dimethylethyl)-4-hydroxyphenyl]-2-[(methylcarbamoyl)ethyl]]-5-[3,5-bis(1,1-dimethylethyl)-4-hydroxyphenyl]-N-methyl-2H-[1,2,3]triazole-4-carboxamide.

A 10 mL round-bottom flask, equipped with magnetic stirrer, reflux condenser and nitrogen bubbler, was immersed in an oil bath and charged with 0.38 g (0.50 mmol) of threo-2-[2-benzenesulfonyl-1-[3,5-bis(1,1-dimethylethyl)-4-hydroxyphenyl]-2-[(methylcarbamoyl)ethyl]]-5-[3,5-bis(1,1-dimethylethyl)-4-hydroxyphenyl]-N-methyl-2H-[1,2,3]triazole-4-carboxamide, 2 mL 2-methoxyethanol and 45 mg (0.70 mmol) of sodium azide. The yellow mixture was heated with stirring for 7 hr in a bath maintained at a temperature of 110° C. The mixture was cooled to room temperature followed by the addition of 3 g ice and 3 mL deionized water. The resulting yellow suspension was stirred at 5° C. for 1 h followed by filtration. The recovered solid was washed with 3×3 mL deionized water and dried at 80°

C. at 25 torr for 3 days to furnish 4-[3,5-bis(1,1-dimethylethyl)-4-hydroxyphenyl]-N-methyl-1H-[1,2,3]triazole-5-carboxamide 0.28 g., of yellow solid, 96.9% purity by HPLC.

Product Analysis

TLC (Rf values on silica gel 60 F 254, E. Merck)
Mobile phase: 1:1 ethyl acetate—hexane

| Compound | Rf |
|---|---|
| (V) | 0.49 |
| (IV) | 0.07 |
| (II) | 0.61 |
| (I) | 0.46 |
| (III) | 0.33 |

Instrument: Perkin Elmer Series 410
Column: Nucleosil C18, 300×4.6 mm, 10μ
Eluent: linear gradient, 20–100% MeCN contg. 0.1% TFA/ 20 min
Flow Rate: 2 mL/min
Temperature: ambient
Detection: UV at 220 and 268 nm
Sample Size: 5 μL at 0.5 mg/mL

| Compound | Retention Time (min) | Wave Length (nm) |
|---|---|---|
| (V) | 7.9 | 220 |
| (IV) | 4.1 | 220 |

-continued

| Compound | Retention Time (min) | Wave Length (nm) |
|---|---|---|
| (II) | 15.4 | 220 |
| (I) | 13.1 | 268 |
| (III) | 17.9 | 268 |

What is claimed is:
1. A compound having the structure

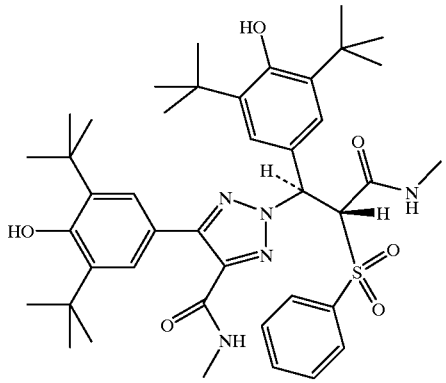

threo-2-[2-benzenesulfonyl-1-[3,5-bis(1,1-dimethylethyl)-4-hydroxyphenyl]-2-[(methylcarbamoyl)ethyl]]-5-[3,5-bis(1,1-dimethylethyl)-4-hydroxyphenyl]-N-methyl-2H-[1,2,3]triazole-4-carboxamide.

* * * * *